United States Patent
Weisbeck et al.

(10) Patent No.: US 6,770,765 B2
(45) Date of Patent: Aug. 3, 2004

(54) CATALYST

(75) Inventors: Markus Weisbeck, Köln (DE); Marie-Therese Heinen, Langenfeld (DE); Jörg Schmitt, Grevenbroich (DE); Gerhard Wegener, Mettmann (DE); Markus Dugal, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/340,289

(22) Filed: Jan. 10, 2003

(65) Prior Publication Data

US 2003/0134741 A1 Jul. 17, 2003

(30) Foreign Application Priority Data

Jan. 15, 2002 (DE) .......................................... 102 01 241

(51) Int. Cl.$^7$ .......................... C07D 301/04; B01J 21/08
(52) U.S. Cl. ...................................... 549/523; 502/243
(58) Field of Search ........................... 549/523; 502/243

(56) References Cited

U.S. PATENT DOCUMENTS

| | | | |
|---|---|---|---|
| 5,354,875 A | 10/1994 | Nemeth et al. | 549/531 |
| 5,623,090 A | 4/1997 | Haruta et al. | 568/360 |
| 5,932,750 A | 8/1999 | Hayashi et al. | 549/523 |
| 5,965,754 A | 10/1999 | Clark et al. | 549/533 |
| 6,031,116 A | 2/2000 | Bowman et al. | 549/523 |
| 6,034,028 A | 3/2000 | Hayashi et al. | 502/243 |
| 6,252,095 B1 | 6/2001 | Hayashi et al. | 549/523 |
| 6,309,998 B1 | 10/2001 | Bowman et al. | 502/242 |
| 6,323,351 B1 | 11/2001 | Bowman et al. | 549/536 |
| 6,362,349 B1 | 3/2002 | Kuperman et al. | 549/533 |
| 2002/0052290 A1 | 5/2002 | Bowman et al. | 502/243 |
| 2002/0115873 A1 | 8/2002 | Stumann et al. | 549/534 |

FOREIGN PATENT DOCUMENTS

| | | |
|---|---|---|
| DE | 199 20 753 | 10/2000 |
| DE | 199 25 926 | 12/2000 |
| DE | 100 23 717 | 11/2001 |
| WO | 00/59632 | 10/2000 |
| WO | 01/41921 | 6/2001 |

OTHER PUBLICATIONS

Ann. Rev. Mater. Sci., 15, (month unavailable) 1985, pp. 227–248, L.C. Klein, "Sol–Gen Processing of Silicates".
Adv. Colloid Interface Sci., 5, (month unavailable) 1976; pp. 245–273, S.J. Teichner, G.A. Nicolaon, M.A. Vicarini and G.E.E. Gardes, "Inorganic Oxide Aerogels".
Catal. Rev. Sci. Eng., 37, (month unavailable) 1995 pp. 515–556, Michael Schneider and Alfons Baiker, "Aerogels in Catalysis".

*Primary Examiner*—Taofiq Solola
(74) *Attorney, Agent, or Firm*—Joseph C. Gil; John E. Mrozinski, Jr.

(57) ABSTRACT

The present invention provides hydro-oxidation catalysts for the oxidation of hydrocarbons, containing an organic-inorganic hybrid material as well as gold particles and/or silver particles, a process for the production thereof, and the use thereof as a catalyst.

8 Claims, No Drawings

CATALYST

FIELD OF THE INVENTION

The present invention provides hydro-oxidation catalysts, for the oxidation of hydrocarbons, containing an organic-inorganic hybrid material as well as gold particles and/or silver particles, a process for the production thereof, and methods of use thereof as a catalyst.

BACKGROUND OF THE INVENTION

Akylene oxides such as propene oxide, for example, can be produced from alkenes such as propene. In this procedure, alkenes are reacted, in the presence of catalysts, with oxygen and with a reducing agent, e.g. hydrogen. This process is termed a hydro-oxidation process and the catalysts used therein are termed hydro-oxidation catalysts (abbreviated herein: HO catalysts).

Purely inorganic catalysts that contain titanium and gold are known for the partial oxidation of hydrocarbons in the presence of oxygen and hydrogen. Catalysts of this type are disclosed, for example, in EP-A 0 709 360, EP-A 0 876 215, EP-A 0 827 779, WO 98/00414, WO 99/43431 and WO 99/52883.

Such catalysts are mainly powdered catalysts produced by multi-stage processes. Suitable powdered support materials, which are generally based on silicon oxide, are impregnated with a titanium precursor, washed, dried and converted in a subsequent process step into insoluble gold hydroxides in the liquid phase by means of gold precipitation by deposition precipitation (soluble gold precursors are converted into insoluble gold hydroxides, by changing the pH from acidic to basic. This means that gold hydroxides are precipitated on the support surface) with gold precursors at a controlled pH.

These so-called precursors are precursor compounds (salts and other compounds).

The powdered material which contains the Ti and Au and which is obtained in this manner cannot yet be used in a fixed bed reactor without a molding step.

Oxidation catalysts which contain noble metals and which are based on organic-inorganic hybrid materials, and a process of producing epoxides from olefins, oxygen and hydrogen using these oxidation catalysts, are known from WO 01/41921. Powdered catalysts are used. Organic-inorganic hybrid materials, which contain titanium are produced by a sol-gel process. The gold content of this hybrid process is imparted in a subsequent impregnation step. This impregnation is termed incipient wetness. Incipient wetness is an impregnation in which an accurately determined amount of solvent is used which corresponds to the pore volume of the support. This gives rise to a sponge effect, in which the support often remains dry on a macroscopic scale.

Similar oxidation catalysts containing noble metals and which are based on organic-inorganic hybrid materials are described in DE-A 101 07 777, but differ from the systems described above in that noble metal particles are deposited on to the finished hybrid materials by spray-drying, namely in a subsequent step comprising a sol-gel process which includes gel work-up. Catalysts which range in size from powders to pellets are obtained (molding size <2 mm) depending on the process.

DE-A 100 23 717 describes oxidation catalysts based on organic-inorganic hybrid materials which have a content of noble metals and which can be used for the production of epoxides from olefins. In a subsequent step, these powdered catalysts are formed into moldings, such as extrudates, granules, pellets, etc.

As an alternative to the molding process described in DE-A 100 23 717 (conversion of organic-inorganic hybrid materials which contain gold and/or silver into moldings using binders, fillers and molding apparatuses such as extrusion presses, extruders, etc.), a route to HO catalysts is known in which an organic-inorganic hybrid material which does not contain noble metals is deposited on the inert moldings by impregnation, and the noble metal is deposited on the impregnated molding in a subsequent step.

All the processes published heretofore have the disadvantage that the catalysts disclosed therein are produced by multi-stage syntheses, and are therefore associated with high manufacturing costs.

For industrial processes, it is desirable to develop catalysts which achieve service lives of industrial interest, whilst exhibiting excellent selectivities and high productivities. Moreover, a pressure drop across the catalyst bed that is as low as possible is desirable. In order to produce catalysts on an industrial scale (a tonnage scale), the process steps for the preparation of the catalysts should be as reproducible and as simple as possible. To achieve an economic process, the cost of catalyst production should be very low.

SUMMARY OF THE INVENTION

Accordingly, the present invention provides catalysts exhibiting low pressure drops for industrial processes, which provide improved selectivities and productivities compared with the prior art.

The present invention further provides a process of producing these highly active catalysts.

The present invention also provides a process of producing these highly active catalysts which is as reproducible as possible.

The highly active catalysts of the present invention have a high mechanical strength.

The present invention yet further provides a process of catalyst production, the cost of which is as low as possible. This is accomplished by having only a few preparation steps and the use of simple apparatus.

The present invention still further provides a catalyst for the oxidation of hydrocarbons.

The present invention greatly reduces or eliminates the disadvantages of known powdered catalysts (high pressure drop in tubular reactors, more rapid deactivation as a result of elevated local catalyst concentration).

The present invention still further provides a technologically simple, gas phase hydro-oxidation process for the selective oxidation of hydrocarbons with a gaseous oxidizing agent and in the presence of a reducing agent on said catalysts, which results in high yields and low costs whilst achieving high catalyst productivities, very high selectivities and catalyst service lives of industrial interest.

DETAILED DESCRIPTION OF THE INVENTION

The present invention will now be described for purposes of illustration and not limitation.

The present invention provides a process for producing a catalyst comprising the provision of a support and impregnation of the support with an organic-inorganic hybrid sol which contains titanium and which contains gold and/or silver.

The process may preferably include modifying the surface of the catalyst with silicon alkyl compounds, silicon aryl compounds and/or SiH compounds.

In this respect, the support may preferably be selected from the group consisting of oxides of silicon, oxides of aluminium, oxides of zirconium, oxides of titanium, oxides of boron, zeolites, clays, mixed oxides of the aforementioned oxides, carbon, activated carbon, carbon black, graphite, monoliths, knitted fabrics, cordierite monoliths, ceramic foams, alkali carbonates, alkaline earth carbonates, carbides, silicon carbide, silicon nitride, metals, glasses and mixtures thereof.

More preferably, the support is selected from the group consisting of alumina, silicon oxide, silicon carbide, carbon and a cordierite monolith.

Most preferably, the support is α-alumina or silicon carbide.

The process may also preferably include an annealing step at temperatures in the range from 100–1000° C., particularly from 200 to 600° C.

The catalyst of the present invention comprises a support, an organic-inorganic hybrid material which is formed from the organic-inorganic hybrid sol, titanium in chemically bound form, and gold particles and/or silver particles.

A preferred organic-inorganic hybrid material for the catalyst of the present invention is based on silicon oxide.

In this respect, the organic-inorganic hybrid material may preferably contain terminal and/or bridging organic groups on the silicon atoms of the organic-inorganic hybrid material.

The catalyst preferably contains gold and silver in the organic-inorganic hybrid material in an amount between 0.001 to 15% by weight.

More preferably, the content of gold in the organic-inorganic hybrid material is 0.001–2% by weight.

The catalyst may also preferably have a content of silver in the organic-inorganic hybrid material between 0.01–15% by weight.

The catalyst preferably may contain gold particles that have a diameter less than 10 nm.

Furthermore, in one embodiment of the present invention the catalyst that comprises other extraneous oxides (termed promoters).

The method of the present invention also provides a process for the selective, partial oxidation of hydrocarbons in the presence of molecular oxygen and of a reducing agent, and in the presence of the catalyst according to the invention.

One preferred process is a process of producing epoxides from alkenes in the presence of molecular oxygen and of a reducing agent and the catalyst according to the invention.

The process in which the epoxide is propene oxide and the alkene is propene is preferred.

The catalyst of the present invention preferably has titanium present as titanium oxide wherein the titanium oxide concentration is 0.1 to 10 mol % with respect to the amount of Si and Ti in the hybrid material.

A process in which silicon hydride units are added during annealing is preferred.

Hereinafter, the support is also termed a molding material. Catalysts according to the invention are hereinafter termed catalyst moldings.

The catalyst moldings according to the invention, which contain organic-inorganic hybrid materials and gold and/or silver particles, have the advantage that moldings of high mechanical strength are obtained. The catalysts which are thus produced are hereinafter also termed hydro-oxidation catalysts (HO catalysts).

Catalysts are described herein for the first time in which the generation of catalytically active titanium and gold species is achieved in a single process step.

The catalysts of the present invention have longer catalyst lifetimes than the original powdered catalysts, whilst maintaining high selectivities and productivities. Moreover, the catalysts according to the invention enable very low pressure drops to be achieved in industrially relevant reactors, such as fixed bed reactors.

HO catalysts are described herein for the first time in which the generation of catalytically active titanium and gold species is achieved in a single process step.

The synthesis of these HO catalysts is surprising, because the gold clusters in the catalyst synthesis according to the invention do not agglomerate to form large, catalytically inactive gold particles.

Further, according to the present invention the simultaneous synthesis of the correct Ti and Au species is effected for the first time on moldings which—optionally after thermal treatment—can be used directly in reactors (e.g. fixed bed reactors). It is thus possible to fulfill the requirement for HO catalysts by efficiently providing catalytically active Ti and Au species on suitable moldings in one process step.

The HO catalysts according to the invention enjoy a considerable economic advantage compared with prior catalysts. Moreover, the systems according to the invention provide a considerably longer catalyst lifetime than that of conventional HO catalysts.

The possibility, for the first-time, of depositing all the requisite HO species by single or multiple impregnation (e.g. spray impregnation, liquid phase impregnation, incipient wetness, etc) on all possible surfaces opens up diverse new OH catalysis reaction routes. Thus not only can palletized, inert moldings for fixed bed reactors be impregnated with HO species, but large surfaces can also be impregnated, such as those of monoliths for example.

The Organic-Inorganic Gels are Described Below.

Organic-inorganic hybrid materials as used in the description of the present invention are organically modified glasses based on silicon oxide, which are preferably produced in sol-gel processes by hydrolysis and condensation reactions of what are generally compounds of low molecular weight, and which contain terminal and/or bridging organic groups—preferably silicon organosilicon groups—in their network, and which advantageously contain free silicon hydride units. These are described in Assignee's copending US applications, Ser. No. 10/149,056 and Ser. No. 10/019,997, which are hereby incorporated in their entireties in the present application by reference.

The catalytically active organic-inorganic hybrid materials which contain titanium and noble metals, and which are subsequently deposited on moldings, preferably contain, with respect to silicon oxide as the base component of the hybrid material, between 0.1 and 20 mol % titanium, preferably between 0.5 and 10 mol %, most preferably between 0.8 and 7 mol %. The titanium is preferably present in the form of an oxide and is preferably chemically incorporated or bonded in the silicon oxide lattice via Si—O—Ti and Si—O—Si bonds. Active catalysts of this type only comprise subordinate Ti—O—Ti domains.

It is assumed that in active catalysts based on organic-inorganic hybrid materials, titanium is bonded to silicon via heterosiloxane bonds.

Apart from titanium, the catalysts can also contain other extraneous oxides, which are termed promoters, namely those of Group 1 of the IUPAC Periodic Table (1985), such as sodium, potassium and caesium, of Group 2, preferably magnesium and calcium, of Group 5, such as vanadium, niobium and tantalum, preferably tantalum, of Group 6, preferably molybdenum and tungsten, of Group 3, preferably yttrium, of Group 4, preferably zirconium, of Group 8, preferably iron, of Group 9, preferably iridium, of Group 12, preferably zinc, of Group 15, preferably antimony, of Group 13, preferably aluminium, boron, thallium, and metals of Group 14, preferably germanium.

The promoters, hereinafter denoted by M, are generally present in dispersed form in the organic-inorganic hybrid material. The chemical composition of these materials can be varied over wide ranges. The proportion of the promoter element with respect to silicon oxide preferably falls within the range from 0 to 10 mol %, more preferably 0 to 3 mol %. As those skilled in the art will appreciate, a plurality of different promoters can also be used. The promoters are preferably used in the form of promoter precursor compounds that are soluble in the respective solvent, such as promoter salts and/or organic promoter compounds and/or organic-inorganic promoter compounds.

These promoters are capable of increasing both the catalytic activity of the organic-inorganic hybrid materials and the service life of the organic-inorganic hybrid materials in catalytic oxidation reactions of hydrocarbons.

If these promoters are incorporated in or added to organic-inorganic hybrid materials which do not contain titanium oxide species, compositions are obtained after thermal activation which exhibit either no catalytic activity or a catalytic activity which is less than that of systems which contain titanium.

The organic-inorganic hybrid materials which contain titanium can be produced either by impregnating an organic-inorganic silicon oxide matrix with a titanium precursor compound, or, preferably, via sol-gel processes. Sol gel production is effected, for example, by mixing suitable compounds, which are usually of low molecular weight, after which the hydrolysis and condensation reaction is initiated by adding water and optionally catalysts (e.g. acids, bases and/or organometallic compounds, electrolytes and/or ultrasound). Conducting sol-gel processes such as these is known in principle to one skilled in the art (L. C. Klein, *Ann. Rev. Mar. Sci.*, 15 (1985) page 227, and S. J. Teichner, G. A. Nicolaon, M. A. Vicarini and G. E. E. Garses, *Adv. Colloid Interface Sci.*, 5 (1976) page 245).

The HO catalysts according to the invention preferably contain the following components on a suitable support: gold and/or silver particles and organic-inorganic hybrid materials that contain Ti and which optionally comprise Si—H groups. In their thermally treated state, the active components can be approximately described by the following empirical formula (I) (radicals formed after modification on the surface and any incompletely reacted groups are not taken into consideration here):

$$SiO_x \cdot Org \cdot H \cdot TiO_y \cdot MO_z \cdot E \qquad (I)$$

wherein $SiO_x$ represents silicon oxide, Org represents the non-hydrolyzable organic constituents formed, preferably by a sol gel process, from the organic-inorganic precursors, H represents the molar proportion of "element"-H groups in the network, wherein "element" does not represent carbon. M represents a promoter, preferably K, Cs, Mg, Ca, Ta, Fe, Mo, Sb, V, Nb, Zr, Al, B, Ti, Y, Ge or combinations thereof, E represents a noble metal, preferably gold and/or silver, and x, y and z represent the effective requisite number of oxygens to saturate the valencies of the organic-inorganic compounds of the inorganic elements Si, Ti, and M.

Composition (I) described above can be varied over a wide range.

With respect to silicon oxide, the proportion of Org in mol percent can range between 0 and 200%. It is preferably between 1 and 200%, more preferably between 10 and 100%. The molar proportion of Si—H units with respect to silicon oxide can vary between 0 and 100 mol %. The proportion preferably ranges between 0.001 and 50%, more preferably between 0.001 and 20 mol %. The proportion of titanium oxide with respect to silicon oxide preferably ranges between 0.1 and 10 mol %, more preferably between 0.5 and 8.0%, most preferably between 0.5 and 7.0%. The proportion of MO with respect to silicon oxide preferably ranges between 0 and 12 mol %. The proportion of E with respect to the gold- and/or silver-free active component composition preferably ranges between 0.001 and 15% by weight. For gold it is preferably between 0.001 and 2% by weight, and for silver it is preferably between 0.01 and 15% by weight.

Suitable precursor compounds for silicon, titanium and promoter species are mixed organic-inorganic compounds that are advantageously suitable for the sol-gel process, or are a combination of corresponding mixed inorganic and organic-inorganic compounds. As used in the description of the present invention, the term "low molecular weight" refers to monomeric or oligomeric compounds. Polymeric precursor compounds of silicon, titanium and promoters are also suitable if they are sufficiently soluble.

The sol-gel process is based on the polycondensation of hydrolyzed, colloidally dissolved mixed metal components (sol) to form a network (gel).

Hydrolysis is effected by mixing hydrolyzable silicon and titanium precursor compounds, optionally diluted in a solvent, with water (simultaneously or in succession). Because under normal conditions the hydrolysis of silicon precursor compounds is slow, catalysts are generally required so that it proceeds more rapidly and completely (J. Livage et al., Chemistry of Advanced Materials: An Overview Edited by: L. V. Interrante et al., VCH, New York, 1998, pages 389–448). The resulting silanols condense to form siloxane compounds. Dissolved polysiloxane networks are thus formed. Branching and crosslinking continue until the polymer is large enough for the gel transition to occur. The gel firstly consists of a solid polymer network that is permeated by a solvent. If the solvent is an alcohol, what are termed alcogels are formed. After ageing, the compositions according to the invention can be dried to form either xerogels, aerogels or cryogels. During drying, e.g. of alcogels, the network shrinks with loss of the solvent, whereupon a xerogel is formed. If the gel is dried under supercritical conditions ("High-Temperature Supercritical Drying" or "Low-Temperature Supercritical Drying"), the resulting network product is termed an aerogel (A. Baiker et al., *Catal. Rev. Sci. Eng.* 1995, 37, pages 515–556); cryogels are obtained when drying is effected by freeze-drying.

The preferred solvents for the sol-gel process are alcohols such as isopropanol, butanol, t-butanol, ethanol or methanol, ketones such as acetone, and ethers such as THF or tert.-butyl methyl ether, for example.

Suitable starting materials include all the soluble silicon and titanium compounds that are known to those skilled in the art and which can be employed as a starting material for the corresponding oxides or hydroxides. Silicon and titanium compounds of formula (II) are preferably used:

$$[R_xM'(OR')_{4-x}] \qquad (II),$$

wherein

M' is selected from silicon and titanium,

R and R' independently represent $C_1$–$C_{12}$ alkyl and $C_6$–$C_{12}$ aryl, wherein x=0, 1, 2 or 3 and R' can also represent H.

In the organically modified silanes, one or more hydrolyzable groups may be replaced by terminal and/or bridged, saturated (e.g. $CH_3$, $C_2H_5$, $C_3H_7$, . . . ) or unsaturated (e.g. $C_2H_3$, $C_6H_5$) R group(s). Mixtures of different organically modified silanes or mixtures of organically modified silanes with purely inorganic silicon network formers, such as tetraalkoxysilanes, can also advantageously be used. Polyfunctional organosilanes, e.g. polysilsesquioxanes (polymethylsilsesquioxanes, polyvinylsilsesquioxanes, . . . ) silanols and alkoxides, can also be used. Silanes, which are optionally organically modified, can also be reacted in the presence of di- or polyhydric alcohols such as 1,4-butanediol, to form organically modified polysiloxanes. In the present invention, bridged R groups (alkylene radicals) are bridged structures such as chain-like, star-shaped (branched), cage-like or ring-like structural elements. "Alkyl" is to be understood to represent all terminal and/or bridged, linear or branched alkyl radicals comprising 1 to 12 carbon atoms which are known to those skilled in the art, such as methyl, ethyl, n-propyl, i-propyl, n-butyl, i-butyl, t-butyl, n-pentyl, i-pentyl, neo-pentyl, hexyl and other homologes, which themselves can be further substituted. Suitable substituents include halogens, nitro, alkyl, hydroxide or alkoxy, as well as cycloalkyl or aryl, such as benzoyl, tris-methylphenyl, ethylphenyl, chloromethyl, chloroethyl and nitromethyl. Nonpolar substituents are preferably used, such as methyl, ethyl, n-propyl, i-propyl, n-butyl, i-butyl, t-butyl and benzoyl.

Higher molecular weight and/or oligomeric organic-inorganic silicon and titanium precursors are also suitable, such as gamma-glycidoxypropyltrimethoxysilane, 3,4-epoxycyclohexyl-ethyl-trimethoxysilane, 1-(triethoxysilyl)-2-(diethoxymethylsilyl)-ethane, tris(gamma)-trimethoxypropylsilyl isocyanurate, peralkylated cyclosiloxanes such as hexamethylcyclotrisiloxane, octamethyltetrasiloxane or decamethylpentasiloxane. Polyalkyl (aryl)siloxanes such as polydimethylsiloxane are also suitable.

"Aryl" is to be understood to include all mono- or polynuclear radicals comprising 6 to 12 carbon atoms which are known to those skilled in the art, such as phenyl, naphthyl or fluorenyl, which themselves may be substituted. Suitable substituents here include a halogen, nitro, alkyl or alkoxyl, as well as cycloalkyl or aryl, such as bromophenyl, chlorophenyl, toluyl and nitrophenyl. Phenyl, fluorenyl, bromophenyl, chlorophenyl, toluyl and nitrophenyl are preferred.

Even though salts such as halides, nitrates and hydroxides can be used, the alkoxides of these elements are preferred, e.g. the n-butoxides, t-butoxides, isopropoxides, n-propoxides, ethoxides and methoxides thereof.

The titanium derivatives which are preferably used are those such as tetralkoxytitanates comprising $C_1$–$C_{12}$ alkyl groups such as iso-butyl, tert-butyl, n-butyl, i-propyl, n-propyl, ethyl, etc., or titanium alkoxy complexes such as those described in U.S. Pat. No. 6,090,961, e.g. ($\eta^5$-tetramethylcyclopentadienyl)3-tert-butyl-5-methyl-2-phenoxy)-dimethylsilyl titanium dimethoxides, other organic titanium species such as titanium acetylacetonate, $Ti(OSiPh_3)_4$, dicyclopentadienyltitanium dihalides, titanium dihalogenodialkoxides, titanium halogenotrialkoxides, or titanium siloxanes such as diethoxysiloxane-ethyl titanate copolymer (available commercially from Gelest Inc). Chlorine is the preferred halogen substituent. Mixed alkoxides of titanium with other elements such as titanium triisopropoxide-tri-n-butyltin oxide can also be used. The titanium precursor compounds can also be used in the presence of complex-forming components such as acetylacetone or ethyl acetoacetate, for example.

The organic-inorganic silicon and titanium precursor compounds can also be used in combination with inorganic network formers such as tetraethoxysilane ($Si(OC_2H_5)_4$), tetramethoxysilane ($Si(OCH_3)_4$) or homologues thereof. Instead of monomeric alkoxides, condensation products thereof can also be used. Examples of the latter which are available commercially include $Si(OC_2H_5)_4$ condensates, for example. Moreover, oligomeric or polymeric systems such as poly(diethoxysiloxane) can be used.

The aforementioned silicon and titanium precursor compounds are reacted in a sol-gel process, preferably in combination with silanes, and contain silicon hydride units. Most silanes that contain silicon hydrides can be represented by formulae (IIIa) or (IIIb):

$$[R_xSiH_y(OR')_{4-(x+y)}] \qquad (IIIa)$$

$$[R_xSiH_y(Hal)_{4-(x+y)}] \qquad (IIIb),$$

wherein

R and R' independently represent $C_1$–$C_{12}$ alkyl and $C_6$–$C_{12}$ aryl, where x=0, 1, 2 or 3 and y=1, 2 or 3, and where R' and R can also represent H.

The silanes containing Si—H can also be generated in situ, e.g. from halosilanes in the presence of reducing agents such as magnesium hydride.

The compounds of formulae (IIIa) and (IIIb) can be replaced, wholly or in part, by other silicon precursor compounds comprising proportions of Si—H units, such as 1,1,3,3-tetramethyidisiloxane, 1,3,5,7-tetramethylcyclo-tetrasiloxane, tri-n-hexylsilane or triphenylsilane.

Examples of silanes include monoalkoxysilanes ($C_1$–$C_{12}$), dialkoxysilanes ($C_1$–$C_{12}$), trialkoxysilanes ($C_1$–$C_{12}$), dialkoxy-monohalogenosilanes ($C_1$–$C_{12}$), monoalkoxy-dihalogenosilanes ($C_1$–$C_{12}$), methylhydrocyclosiloxane, trihalogenosilanes, dihalogen-silanes and monohalogenosilanes.

Apart from low molecular weight precursors, oligomeric and polymeric precursors which contain silicon hydride can also be used, such as poly(methylhydrosiloxanes).

The preferred trialkoxysilanes are those which comprise $C_1$–$C_{12}$ groups, such as trimethoxysilane, triethoxysilane, triisopropoxysilane, tripropoxysilane, triisopropoxysilane, tributoxysilane, and those which comprise oligomeric or polymeric SiH components, such as poly (methylhydrosiloxane).

The sequence of operations during sol-gel synthesis is not fixed. The HO catalysts according to the invention are generated, for example, by the simultaneous hydrolysis and/or condensation of Si and Ti precursors or by the complete or partial reaction of silicon precursor compounds with water or with catalytic amounts of water and subsequent addition of the corresponding Ti compounds.

In one embodiment of the present invention, the organic-inorganic silicon precursor compound is placed in a vessel, is initially or completely hydrolyzed with water with the addition of a catalyst, and the Ti precursor compound is subsequently added. The addition of silanes comprising free silane-hydride units is likewise not a fixed procedure. The SiH species can be added either before or after the addition of Ti.

According to the invention, gel formation is effected directly on the support surface. One or more treatments of the moist and/or already dried gel with an excess of water or water vapor can optionally be effected in order to complete the hydrolysis and condensation reactions.

The subsequent treatment of the "gel on support" system is not fixed. It can be dried (e.g. at 20–150° C. in an air current or in other atmospheres) and then annealed (150 to 450° C. in air, $N_2$, $H_2$, or in other atmospheres). The freshly impregnated molding can also be annealed directly, without drying.

The hydrophobic character of the organic-inorganic hybrid materials according to the invention is essentially determined by the number and type of terminal and bridging Si—C bonds. Compared with other organic bonds, such as Si—O—C bonds for example, terminal and bridging Si—C bonds have the additional advantage of being substantially chemically inert, i.e. are insensitive to hydrolysis and oxidation reactions.

The Noble Metals (Gold and/or Silver) are Described Below.

In addition to the Si, Ti and possible promoter species, the HO catalysts according to the invention additionally contain noble metal clusters.

The noble metals are added in the form of precursor compounds, such as salts, organic complexes or compounds, or as colloids, preferably during the sol-gel process. Alternatively, sol-gel-modified moldings can also be covered in a previous or subsequent step with noble metal clusters (e.g. by precipitation, impregnation in solution, incipient wetness, spray drying, sputtering, colloids, CVD).

The noble metals are preferably gold and/or silver. In their catalytically active form, the moldings contain gold and/or silver particles which mainly have a particle size of <15 nm. In their catalytically active state, the gold and/or silver mainly exist as the elemental metals (analysis by X-ray absorption spectroscopy). Small proportions of gold and/or silver can also be present in a higher oxidation state. The gold and silver are preferably present as gold and/or silver clusters on a nanometer scale.

The gold particles preferably have a diameter within the range from 0.5 to 50 nm, more preferably 0.8 to 15 nm, and most preferably 0.8 to 10 nm.

The silver particles preferably have a diameter within the range from 0.5 to 100 nm, more preferably 0.5 to 40 nm, and most preferably 0.5 to 20 nm.

It has been found that the selective hydro-oxidation reaction described above is very sensitive to the structure of the catalyst. In the presence of nano-dispersed gold and/or silver particles in or on HO catalyst moldings, an advantageous increase in productivity to form the selective oxidation product has been observed.

With respect to the solid formed from the sol after hydrolysis/condensation/annealing, the gold concentration in the sol which contains silicon and titanium and with which the support is treated is preferably within the range from 0.001 to 2% by weight, preferably 0.001 to 1.5% by weight, and more preferably 0.005–1.0% by weight.

The silver concentration should fall within the range from 0.005 to 20% by weight, preferably 0.01 to 15% by weight, and more preferably from 0.1 to 10% by weight of silver.

For economic reasons, the noble metal content should be the minimum required to prolong the maximum catalyst activity.

The production of the noble metal particles in the organic-inorganic hybrid sol that contains silicon and titanium or on the molding which is treated with the hybrid sol that contains noble metals is not restricted to one method.

The catalytically active noble metal clusters can be generated either by reducing agents and/or by thermal treatment.

Nano-scale gold particles may preferably be produced by thermal treatment in the presence of reducing agents.

Nano-scale silver particles may preferably be produced by thermal treatment in the presence of reducing agents.

It has surprisingly been found that the organic-inorganic hybrid materials which contain proportions of hydrogen silanes are particularly suitable for depositing metals such as gold and silver, with a high degree of dispersion, on external and internal surfaces. Ultrafine metal particles are generated in the course of this procedure.

In contrast, on purely inorganic silica or $SiO_2$—$TiO_2$ mixed oxide surfaces (analogous to WO98/00415, WO-98/00414, WO-98/00413, EP-A 0 827 779), i.e. without organic modification and/or without proportions of hydrogen silanes, it is possible to synthesize nano-scale metal particles with a very narrow particle size distribution, but in a much less selective manner.

The Impregnation of the Support with the Sol is Described Below.

The methods by which the organic-inorganic hybrid sol with a content of noble metal precursors and/or noble metal colloids are deposited on suitable supports are not subject to any restrictions.

Different catalysts can be produced depending on the method selected.

Impregnating the support in a liquid phase often results in moldings which are impregnated homogeneously. Using dip coating (immersion) or spray impregnation, systems can be generated which cover the entire range from homogeneously impregnated to those comprising shell-like impregnation.

The type of HO catalysts is also essentially determined by the viscosity of the hybrid sol which contains noble metals. In addition to the amount of solvent, the viscosity is also affected by the ageing of the sol-gel. A liquid, low-viscosity sol-gel system is preferably deposited on the molding.

Impregnation of the molding with the hybrid sol can be effected as a single- or multi-stage process.

The amount of hybrid sol on the support is not fixed. In many cases, the proportion of active ingredient after annealing ranges from 1 to 80%, preferably 1 to 60%, most preferably 3 to 30%.

The further processing of the impregnated molding is not fixed. Excess hybrid sol can be removed or gelled by a plurality of routes, e.g. by drying, by vacuum treatment, in a centrifuge, in an air current, or by similar routes.

Impregnation of the moldings with the hybrid sol can be conducted not only in a single step, i.e. using hybrid sols containing noble metals, but can also be conducted in two steps, by firstly impregnating the moldings with HO hybrid sols which are free from noble metals and subsequently covering them with noble metals or noble metal precursors, or vice versa.

The catalytic activity of the HO catalysts according to the invention is often increased by subsequent thermal treatment.

The Annealing Procedure is Described Below.

The HO catalysts according to the invention are advantageously activated, before and/or after impregnation or immersion with the hybrid sols containing noble metals, by thermal treatment at temperatures within the range from 100–1000° C. in different atmospheres such as air, nitrogen, hydrogen, carbon monoxide or carbon dioxide.

Thermal activation is preferably effected at temperatures within the range from 150–400° C. in gases which contain oxygen, such as air, oxygen-hydrogen or oxygen-inert gas mixtures or combinations thereof, or at temperatures within the range from 150–1000° C. under inert gases such as nitrogen and/or hydrogen and/or inert gases or combinations thereof. Activation of the organic-inorganic hybrid materials is most preferably effected under inert gases within the temperature range from 200–600° C.

It may also be advantageous, however, to impregnate the moldings with hybrid sols which are free from noble metals, to anneal them at temperatures within the range from 200–1000° C. and subsequently to cover them with noble metal. The thermally activated (annealed) catalysts often exhibit a significantly higher catalytic activity and a prolonged service life compared with known catalysts.

The Supports are Described Below.

The selection of the support for the synthesis of the HO catalyst moldings is subject to no particular restriction as regards material, particle size, mechanical strength, size of surface, pore structure, absorption capacity, chemical inertness, etc., provided that it is possible effectively to impregnate said sols with the HO hybrid sols which contain noble metals, and provided that the support used does not give rise to secondary or subsequent reactions of the desired products.

The preferred supports are mechanically stable, chemically inert, commercially available in industrial quantities and inexpensive. Particulate supports are particularly advantageous, and are used in the form of spheres, cylinders, hollow cylinders, saddles, extrudates, hollow extrudates, granules or rods, for example.

Particulate catalyst moldings can be used in the form of a fixed bed of loose material or in the form of a fluidized bed. Instead of being deposited on a particulate support, the hybrid sol that contains noble metals can be deposited on monolithic support systems, for example. Examples thereof include ceramic honeycomb bodies (such as cordierite honeycomb bodies), ceramic sponges, knitted fabrics, etc.

The particle size depends on how the reaction is conducted, e.g. in a fixed bed or fluidized bed, on the quantitative throughput, and on the type and size of the reactor. If a fixed bed reactor is used, a low pressure drop, good heat transfer and a low diffusion barrier are attained for moldings of sizes 2–10 mm. In fluidized bed processes, mechanically stable supports with a narrow particle size distribution of 50–300 $\mu$m are preferred.

All materials that form mechanically stable moldings and which are inert or which only exhibit a slight activity with regard to gas phase oxidation can be used as supports. Suitable examples include oxides of aluminium ($\alpha$-, $\gamma$-, etc.), silicon and zirconium. Carbon in various states, such as activated carbon, carbon black or graphite, can also be used. Carbides such as silicon carbide, or nitrides such as silicon nitride, are also suitable. Glasses and metals of all types can also be used.

In principle, there is no restriction on the size and type of the surface of these moldings. The specific surface is advantageously 0.01–1000 $m^2$/g, more advantageously 0.01–200 $m^2$/g and most advantageously 0.01–100 $m^2$/g.

The pore structure can be micro-, meso- and/or macroporous. Both amorphous and crystalline molding systems can be selected.

In some situations, particularly in order to achieve isothermal reaction conditions, it may be advantageous if the catalyst material is diluted uniformly or in layers with an inert or low-activity molding material. There is no restriction on the choice of dilution materials such as these. Examples include oxides of silicon, aluminum, zirconium, and materials made of glass such as coarse powder, spheres, etc. Silicates, ceramics, carbon and mineral particles are also suitable. By conducting the reaction isothermally, hot spots are often reduced, which has a favorable effect on the service life of the catalysts according to the invention. Moldings that have good thermal conductivities, such as graphite, carbon black and silicon carbide, for example, also reduce hot spots.

The Modification of the Catalyst Surface is Described Below.

The catalytic activity of the catalysts according to the invention can often be increased by modifying the surface.

In the present invention, modification is to be understood in particular as the provision of groups selected from silicon-alkyl, silicon-aryl, silicon hydride, or alkyl or aryl groups which contain fluorine, on the surface of the supported composition, wherein these groups are often covalently or coordinately bonded to the functional groups (e.g. OH groups) on the surface. Any other surface treatment is also expressly included in the scope of the invention, however.

The catalyst surface can be modified in many ways. The moldings can be modified either before impregnation with HO-active components or after impregnation. In some situations, modification before impregnation is preferred.

Modification is preferably effected with organosilicon compounds and/or with organosilicon compounds that contain fluorine and/or with organic compounds which contain SiH, wherein organosilicon compounds and compounds which contain SiH compounds are preferred.

Suitable organosilicon compounds include all silylating agents which are known to those skilled in the art, such as organic silanes, organic silylamines, organic silylamides and derivatives thereof, organic silazanes, organic siloxanes and other organosilicon compounds, which of course can also be used in combination. The term "organosilicon compounds" also expressly includes compounds of silicon and partially fluorinated or perfluorinated organic radicals.

Particular examples of organic silanes include chlorotrimethylsilane, dichlorodimethylsilane, chlorobromodimethylsilane, nitrotrimethylsilane, chlorotrimethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloro-propyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane and 3-cyano-propyidimethylchlorosilane.

Silanes which contain SiH, for example tri-, di- and monoalkoxysilanes, poly(methylhydrosiloxane), etc., are also suitable for surface modification.

Particular examples of organic silylamines include N-trimethylsilyldiethylamine, pentafluorophenyldimethylsilylamine, N-trimethylsilylimidazoles, N-t-butyidimethylsilylimidazole, N-dimethylethylsilylimidazole, N-dimethyl-n-propylsilylimidazole, N-dimethylisopropylsilylimidazole, N-trimethylsilyidimethylamine, N-trimethylsilylpyrrol, N-trimethylsilylpyrrolidine, N-trimethylsilylpiperidine and 1-cyanoethyl(diethylamino)dimethylsilane.

Particular examples of organic silylamides and derivatives thereof include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyl-trifluoroacetamide, N-methyl-N-trimethylsilylheptafluorobutyramide, N-(t-butyldimethylsilyl)-N-trifluoroacetamide and N,O-bis(diethylhydrosilyl)trifluoroacetamide.

Particular examples of organic silazanes include hexamethyldisilazane, heptamethyldisilazane, 1,1,3,3-tetramethyidisilazane, 1,3-bis(chloromethyl)tetramethyidisilazane, 1,3-divinyl-1,1,3,3-tetramethyldisilazane and 1,3-diphenyltetramethyidisilazane.

Examples of other organosilicon compounds are N-methoxy-N,O-bistrimethylsilyltrifluoracetamide, N-methoxy-N, O-bistrimethylsilyl carbamate, N,O-bistrimethylsilyl sulphamate, trimethylsilyltrifluoromethane sulphonate and N,N'-bistrimethylsilylurea.

The preferred silylation reagents are hexamethyidisilazane, hexamethyldisiloxane, trialkoxysilanes, N-methyl-N-(trimethylsilyl)-2,2,2-trifluoroacetamide (MSTFA) and trimethylchlorosilane.

The Process Parameters are Described Below.

The HO catalyst moldings are preferably used in gas phase reactions for the partial oxidation of hydrocarbons in the presence of oxygen and hydrogen.

The process parameters for this hydro-oxidation reaction can be varied over wide ranges.

The catalyst moldings according to the invention are employed in particular at temperatures of 100 to 300° C., preferably 140 to 270° C. and more preferably 160 to 250° C.

For gas phase reactions, it is often advantageous for economic reasons and for reasons relating to the construction of the apparatus to operate under elevated reaction pressures. The contact catalysts according to the invention exhibit particularly high catalytic activities over the pressure range from normal pressure to 70 bar. A pressure level of 2 to 50 bar is preferred, more preferably from 3 to 30 bar.

The residence time can also be varied over a wide range. The residence time is advantageously <70 seconds. The HO catalyst moldings exhibit particularly high catalytic activities at residence times <20 sec, for example at 0.001 to 10 seconds. The present invention also expressly relates to extremely short residence times of the order of milliseconds (<0.001 seconds).

The amount of feed gas or circulating gas, and thus the catalyst loading, is not fixed. In particular, the catalyst loading ranges from 1 to >1000 1 gas/(g active substance× h), preferably from 4 to 600 1 gas/(g catalyst×h), more preferably from 10–500 1 gas/(g active substance×h). The present invention likewise expressly relates to extremely high catalyst loadings, often associated with short catalyst contact times.

The Feed Composition is Described Below.

HO catalyst moldings are preferably used in gas phase reactions for the partial oxidation of hydrocarbons in the presence of oxygen and hydrogen.

In reactions such as these, epoxides are obtained selectively from olefins, ketones are selectively obtained from saturated secondary hydrocarbons, and alcohols are selectively obtained from saturated tertiary hydrocarbons.

The term "hydrocarbon" is to be understood to include unsaturated or saturated hydrocarbons such as olefins or alkanes which may also contain heteroatoms such as N, O, P, S or halogens. The organic component to be oxidized can be acyclic, monocyclic, bicyclic or polycyclic and can be monoolefinic, diolefinic or polyolefinic. In organic components that contain two or more double bonds, the double bonds may be conjugated or unconjugated. The hydrocarbons which are preferably oxidized are those from which oxidation products are formed at a partial pressure which is low enough for the product to be continuously removed from the catalyst. Unsaturated and saturated hydrocarbons are preferred which contain 2 to 20, preferably 2 to 10 carbon atoms, particularly ethene, ethane, propene, propane, isobutane, isobutylene, 1-butene, 2-butene, cis-2-butene, trans-2-butene, 1,3-butadiene, pentene, pentane, 1-hexene, 1-hexane, hexadiene, cyclohexene and benzene.

The molar amount of hydrocarbon used with respect to the total number of moles of hydrocarbon, oxygen, hydrogen and dilution gas, as well as the relative molar ratios of the components, can be varied over wide ranges. An excess of hydrocarbon is preferably used with respect to the oxygen used (on a molar basis). The hydrocarbon content is typically greater than 1 mol % and less than 80 mol %. Hydrocarbon contents within the range from 4 to 90 mol % are preferably used, and are more preferably within the range from 8 to 70 mol %.

Oxygen can be used in very different forms, such as molecular oxygen, air, nitrogen oxide or hydrogen peroxide. Molecular oxygen is preferred.

The mole fraction of oxygen with respect to the total number of moles of hydrocarbon, oxygen, hydrogen and dilution gas can be varied over a wide range. Oxygen is preferably used in a molar deficit with respect to the hydrocarbon. Oxygen is preferably used within the range of 1–30% oxygen by volume, more preferably 5–25% oxygen by volume.

In the absence of hydrogen, the moldings according to the invention only exhibit a slight activity and selectivity. In general, the productivity in the absence of hydrogen is low up to 180° C. At temperatures above 200° C., larger amounts of carbon dioxide are formed in addition to partial oxidation products.

Any known source of hydrogen can be used, such as pure hydrogen, cracker hydrogen, synthesis gas or hydrogen from the dehydrogenation of hydrocarbons and alcohols. In another embodiment of the invention, the hydrogen can also be produced in situ in an upstream reactor, e.g. by the dehydrogenation of propane or isobutane or of alcohols such as methanol or isobutanol. Hydrogen can also be introduced into the reaction system as a complex-bonded species, e.g. as a catalyst-hydrogen complex.

The mole fraction of hydrogen with respect to the total number of moles of hydrocarbon, oxygen, hydrogen and dilution gas, can be varied over a very wide range. Typical hydrogen contents are greater than 0.1% by volume, preferably within the range from 4–80% by volume, more preferably within the range from 5–75% by volume.

A dilution gas such as nitrogen, helium, argon, methane, carbon dioxide, carbon monoxide, or similar gases that mainly exhibit inert behavior, can also optionally be used in addition to the essential gaseous starting materials described above. Mixtures of the inert components described above can also be used. Other inert hydrocarbons, such as fluorinated hydrocarbons (hexafluorethane, $CF_4$, etc.) can also be used as components for diluting the feed or circulating gas. The addition of an inert component has a favorable effect on the transport of the heat evolved from the exothermic oxidation reaction and is often desirable for reasons of safety.

If the process according to the invention is conducted in the gas phase, gaseous dilution components such as nitrogen, helium, argon, etc. are preferably used.

When the invention is carried out in a liquid phase, an inert liquid which is stable to oxidation and which is thermally stable is advisedly used (e.g. alcohols, polyalcohols, polyethers, halogenated hydrocarbons, silicone oils).

The catalysts according to the invention are also suitable for the oxidation of hydrocarbons in the liquid phase. For example, olefins are converted to epoxides in a highly selective manner on the catalysts described above in the liquid phase, either in the presence of organic hydroperoxides, in the presence of hydrogen peroxide, or in the presence of oxygen and hydrogen.

It has surprisingly been found, compared with all the HO catalyst systems which were known hitherto for the catalytic partial oxidation of unsaturated and saturated hydrocarbons, that the catalysts according to the invention often exhibit a catalytic activity and a catalyst service life which are higher by several orders of magnitude.

The catalysts according to the invention can be produced inexpensively on an industrial scale, without process technology problems.

Catalysts which may have become slightly deactivated after months of use can often be regenerated either thermally or by washing them with suitable solvents such as alcohols or water, or by treating them with hot steam or dilute hydrogen peroxide solutions (e.g. a 3–10% solution of $H_2O_2$ in methanol).

The present invention is illustrated by the examples given below. The present invention is not limited to these examples.

EXAMPLES
Procedure for Testing HO Catalyst Moldings (Test Procedure)

A metal tube reactor was used which had an inside diameter of 10 mm and a length of 20 cm, and which was heated at a controlled temperature by means of a thermostat. The reactor was supplied with the gaseous starting materials (propene, oxygen, hydrogen) by a set of three mass flow controllers.

The reactor contained a HO catalyst molding (containing 0.5 g of a catalytically active HO component) at 180° C. and 2 bar pressure. The gaseous starting materials were metered into the reactor from above. The standard catalyst loading was 5 liters of gas per gram of HO molding per hour.

A gas stream of the following composition (hereinafter called the standard gas composition) was used for carrying out oxidation reactions:

$H_2/O_2$/propene: 60/10/30% by volume.

The reaction gases were quantitatively analyzed by gas chromatography. Separation by gas chromatography of the individual reaction products was effected by a combined FID/TCD method in which the gas flowed through three capillary columns:
FID: HP-Innowax, 0.32 mm inside diameter, 60 m log, 0.25 $\mu$m layer thickness.
WLD: A series arrangement of HP-Plot Q, 0.32 mm inside diameter, 30 m long, 20 $\mu$m layer thickness HP-Plot molecular sieve 5 A, 0.32 mm inside diameter, 30 m long, 12 $\mu$m layer thickness.

The abbreviations have the following meanings:
FID: flame ionization detector
TCD: thermal conductivity detector
HP-Plot Q: gas chromatography column supplied by Hewlett Packard (fused silica; PLOT=porous layer open tubular)
HP-Plot molecular sieve 5 A: gas chromatography column supplied by Hewlett Packard (5 Angstrom molecular sieve; PLOT=porous layer open tubular)

Preparation of Hybrid Sol-Gel Solution 1

13.3 g methyltrimethoxysilane (98.1 mmol), 0.33 g triethoxysilane (2 mmol) and 1.15 g tetrapropoxy-titanium (4 mmol), dissolved in 7 g ethanol (absolute, analytical quality), were placed in a vessel, mixed with 2.9 g of an 0.1 N solution of p-toluenesulphonic acid in water and the mixture was stirred for 10 min. 2 g of a 1% solution of gold ($HAuCl_4 \times 3H_2O$ in ethanol) were then added with stirring.

Preparation of Hybrid Sol-Gel Solution 2

This preparation was effected analogously to the preparation of hybrid sol-gel 1, except that 11.56 g methyltrimethoxysilane (85 mmol) and 1.97 g tetramethoxysilane (13 mmol) were used instead of 13.3 g methyltrimethoxysilane (98.1 mmol).

Preparation of Hybrid Sol-Gel Solution 3

This preparation was effected analogously to the preparation of hybrid sol-gel 1, except that 2 g of a 2% gold solution ($HAuCl_4 \times 3H_2O$ in ethanol) were used.

Molding Impregnation; Variant 1:

Preparation of an HO catalyst molding by impregnating commercially available moldings with a hybrid sol-gel solution by dip coating.

The hybrid-sol-gel was in placed in a 100 ml glass beaker. 15 g moldings—pelletised moldings were placed in a sieve with a mesh aperture of 0.5 mm—were immersed for 30 seconds in a hybrid sol-gel solution, excess sol-gel was removed in a centrifuge (when monoliths were used, excess sol-gel was removed by means of compressed air), dried for 1 hour at room temperature and subsequently annealed for 4 hours at 400° C. under nitrogen. The molding contained about 3% by weight of HO-active components.

To test the HO catalyst moldings by the procedure given above, 16 g of the catalyst moldings obtained in this manner, corresponding to about 0.5 g of HO-active substance, were used as a fixed bed catalyst.

Molding Impregnation; Variant 2:

Preparation of a HO catalyst molding by spray-impregnating commercially available moldings with a HO hybrid sol-gel solution.

15 g of palletized moldings were placed in a drum (made of a plastics material, 15 cm diameter, inclined at 30°, 50 rpm). The hybrid sol-gel solution was sprayed on to the rotating molding particles by means of a fine nozzle. After drying for 1 hour at 25° C., the material was annealed for 4 hours at 400° C. under nitrogen. The molding contained about 3% by weight of HO-active components.

In order to test the HO catalyst moldings by the procedure given above, 16 g of the catalyst moldings obtained in this manner, corresponding to about 0.5 g of HO-active substance, were used as a fixed bed catalyst.

The following Table gives the results obtained using the catalysts according to the invention (no comparative tests are given in the Table). (The supports were supplied by Condea, of Hamburg)

| Ex. No. | Moldings | Hybrid sol-gel method | Molding impregnation method | PO selectivity [%] | Productivity gPO/(kgWS* × h) after 48 h | 7 days |
|---|---|---|---|---|---|---|
| 1 | α-Al$_2$O$_3$ spheres, 2 mm spheres, supplied by Condea, Batch No. TKA 306 | 1 | 1 | 95 | 200 | 183 |
| 2 | α-Al$_2$O$_3$ spheres, 2 mm spheres, supplied by Condea, Batch No. TKA 306 | 1 | 2 | 95 | 250 | 230 |
| 3 | α-Al$_2$O$_3$ spheres, 2 mm spheres, supplied by Condea, Batch No. TKA 306 | 2 | 2 | 95 | 265 | 250 |
| 4 | α-Al$_2$O$_3$ hollow extrudate, 3–4 mm extrudate, supplied by Condea, Batch No. M908 | 1 | 2 | 95 | 185 | 170 |
| 6 | α-Al$_2$O$_3$ spheres, 2–4 mm spheres, supplied by Procatalyse, Description SPH 512, | 1 | 2 | 95 | 140 | 120 |
| 7 | α-Al$_2$O$_3$ spheres, 2–4 mm spheres, supplied by Procatalyse, Type SPH 512 | 3 | 2 | 95 | 180 | 140 |
| 8 | SiC spheres, 3 mm spheres, supplied by Norton, Type XC 69374 | 1 | 2 | 96 | 230 | 220 |
| 9 | SiC spheres, 3 mm spheres, supplied by Norton, Type XC 69374 | 2 | 2 | 96 | 240 | 220 |
| 10 | Cordierite honeycomb body, supplied by Dow Corning | 3 | 1 | 96 | 200 | 190 |
| 11 | Metal wire grid rings, 4 mm | 1 | 1 | 95 | 150 | 145 |

WS = HO-active substance

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a catalyst comprising
providing a support, and
impregnating the support with an organic-inorganic hybrid sol containing titanium and at least one of gold and silver.

2. The process according to claim 1, further including modifying the surface of the catalyst with silicon alkyl compounds, silicon aryl compounds and/or SiH compounds.

3. The process according to claim 1, wherein the support is selected from the group consisting of oxides of silicon, oxides of aluminium, oxides of zirconium, oxides of titanium, oxides of boron, zeolites, clays, mixed oxides of the aforementioned oxides, carbon, activated carbon, carbon black, graphite, monoliths, knitted fabrics, cordierite monoliths, ceramic foams, alkali carbonates, alkaline earth carbonates, carbides, silicon carbide, silicon nitride, metals, glasses and mixtures thereof.

4. The process according to claim 3, wherein the support is selected from the group consisting of alumina, silicon oxide, silicon carbide, carbon and cordierite monolith.

5. The process according to claim 4, wherein the support is α-alumina or silicon carbide.

6. The process according to claim 1, further including an annealing step at temperatures within the range from 100–1000° C.

7. The process according to claim 6, wherein the annealing is effected at temperatures within the range from 200–600° C.

8. The process according to one of claim 6 or 7, wherein silicon hydride units are added during annealing.

* * * * *